(12) United States Patent
Zhou et al.

(10) Patent No.: US 8,835,670 B2
(45) Date of Patent: Sep. 16, 2014

(54) METHOD FOR SYNTHESIS OF LACTIC ACID AND ITS DERIVATIVES

(71) Applicant: Microvast New Materials (Huzhou) Co., Ltd., Huzhou (CN)

(72) Inventors: Xiaoping Zhou, Huzhou (CN); Rui Bi, Huzhou (CN)

(73) Assignee: Microvast Power Systems Co., Ltd., Huzhou, Zhejiang Province (CN)

( * ) Notice: Subject to any disclaimer, the term of this patent is extended or adjusted under 35 U.S.C. 154(b) by 0 days.

(21) Appl. No.: 13/727,589

(22) Filed: Dec. 26, 2012

(65) Prior Publication Data

US 2014/0058130 A1    Feb. 27, 2014

(30) Foreign Application Priority Data

Aug. 27, 2012 (CN) .......................... 2012 1 0307028

(51) Int. Cl.
*C07C 69/68*     (2006.01)
*C07C 51/00*     (2006.01)

(52) U.S. Cl.
USPC ......................................... 560/179; 562/515

(58) Field of Classification Search
CPC .......... C07C 69/68; C07C 59/08; C07C 51/00
See application file for complete search history.

(56) References Cited

U.S. PATENT DOCUMENTS

2013/0204036 A1 *   8/2013   Tominaga et al. ............ 560/179

FOREIGN PATENT DOCUMENTS

GB            467510      * 12/1935
WO    WO 2011/125882 A1  * 10/2011

* cited by examiner

*Primary Examiner* — Paul A Zucker
(74) *Attorney, Agent, or Firm* — Cheng-Ju Chiang

(57) ABSTRACT

A method for synthesis of lactic acid and its derivatives is provided. First, a mixture is prepared, which includes: at least one carbohydrate-containing raw material, at least one alcohol, at least one composite catalyst containing metal chloride(s) ($MCl_n$) and tin-containing compound(s), and at least one solvent, wherein M is selected from a group consisting of $Li^+$, $Na^+$ $K^+$, $Mg^{2+}$, $Ca^{2+}$, $Sr_{2+}$, $Ga^{3+}$, $In^{3+}$, $Sb^{3+}$, $Bi^{3+}$, $Cr^{3+}$, $Mn^{2+}$, $Fe^{2+}$, $Co^{2+}$, $Ni^{2+}$, $Zn^{2+}$, and n represents 1, 2 or 3. Then, the mixture is heated to obtain lactic acid and its derivatives. By using the above catalyst and method, it is capable of converting carbohydrate-containing raw material to lactic acid and its derivatives directly in a more efficient and economical way.

17 Claims, 2 Drawing Sheets

METHOD FOR SYNTHESIS OF LACTIC ACID AND ITS DERIVATIVES

FIELD OF THE INVENTION

This invention generally relates to a method for synthesis of lactic acid and its derivatives.

BACKGROUND OF THE INVENTION

Glucose, sugarcane, starch, and celluloses are the most abundant renewable carbon sources found naturally on the earth. The high content of oxygenated functional groups in these carbohydrates has advantages in making use of them to produce fundamental chemicals. In particular, these carbohydrates are the most attractive feedstocks for intermediate chemical production in a sustainable way without emitting $CO_2$.

Theoretically, two moles of lactic acid could be obtained from one mole of hexose either by fermentation or by catalytic reaction. Lactic acid itself is a monomer for the biodegradable polylactate synthesis. Lactic acid and its derivatives (such as alkyl lactates and polylactate) could act as platform compounds for the synthesis of other carbon-3 building blocks, such as propylene glycol, acrylic acid, and allyl alcohol for the productions of polymers.

Lactic acid is produced by the fermentation of glucose in present chemical industry. FIG. 1 shows the scheme for lactic acid and its derivatives preparation according to a commercial fermentation process. In the fermentation process, the concentration of lactic acid in the obtained water solution is very low. For example, the weight ratio of the lactic acid may be less than 10%. In addition, to isolate the lactic acid from the water solution, $Ca(OH)_2$ should be added into the water solution, and $Ca(OH)_2$ reacts with lactic acid thereby producing calcium lactate solid. Then, the calcium lactate solid is separated and added into $H_2SO_4$ solution. Accordingly, lactic acid is obtained, and $CaSO_4$ solid precipitates in the lactic acid. Obviously, in the fermentation process described above, huge amounts of waste water and $CaSO_4$ solid waste was produced, and only glucose can be used as the feedstock. Lactic acid could be produced from glucose in large scale (120,000 tons/year) in the existing fermentation processes. However, the biological processes generally suffer from low reaction rates and low product concentration (in water), resulting in long reaction times, larger reactors, and high energy consumption in the product purification process (Fermentation of Glucose to Lactic Acid Coupled with Reactive Extraction: Kailas L. Wasewar, Archis A. Yawalkar, Jacob A. Moulijn and Vishwas G. Pangarkar, Ind. Eng. Chem. Res. 2004, 43, 5969-5982).

It is known that, in the presence of aqueous alkali hydroxides, monosaccharides can be converted to lactic acid (R. Montgomery, Ind. Eng. Chem, 1953, 45, 1144; B. Y. Yang and R. Montgomery, Carbohydr. Res. 1996, 280, 47). However, the stoichiometric amount of base ($Ca(OH)_2$) and acid ($H_2SO_4$) in the lactic acid recovery process would be consumed and, therefore, the stoichiometric amount of salt waste would be produced.

Although the commercial fermentation approach can produce large scale lactic acid, it only uses starch as a feedstock and the starch must be prehydrolyzed (or through fermentation) to glucose in advance. The fermentation process produces large amounts of waste water and solid waste ($CaSO_4$). And the fermentation process for producing lactic acid includes many steps, which consume substantial amounts of energy. The infrastructure of the fermentation process is very complicated and uneconomical.

SUMMARY OF THE INVENTION

It is desired to have a process to convert carbohydrate-containing raw material to lactic acid and its derivatives in a more efficient and economical way.

A method for synthesis of lactic acid and its derivatives is provided. First, a mixture is prepared, which includes: at least one carbohydrate-containing raw material, at least one alcohol, at least one composite catalyst containing metal chloride(s) ($MCl_n$) and tin-containing compound(s), and at least one solvent, wherein M is selected from a group consisting of $Li^+$, $Na^+$ $K^+$, $Mg^{2+}$, $Ca^{2+}$, $Sr_{2+}$, $Ga^{3+}$, $In^{3+}$, $Sb^{3+}$, $Bi^{3+}$, $Cr^{3+}$, $Mn^{2+}$, $Fe^{2+}$, $Co^{2+}$, $Ni^{2+}$, $Zn^{2+}$, and n represents 1, 2 or 3. Then, the mixture is heated to obtain lactic acid and its derivatives.

The above described method employs a non-fermentation technique to process carbohydrate-containing raw material and obtain lactic acid and its derivatives directly. Compared with conventional commercially employed fermentation process, less waste water and solid wastes are produced and thus it is more environment-friendly. In addition, the utilization rate of the carbohydrate-containing raw material is improved and the newly proposed process also has the advantages of simplified steps and low energy consumption, and therefore the method is an economical and efficient method.

DETAILED DESCRIPTION OF PREFERRED EMBODIMENTS

The detailed descriptions of the present invention set forth below in connection with the examples are preferred embodiments of the present invention, but the present invention is not limited to the embodiments and forms described hereinafter.

This disclosure provides a catalyst for synthesis of lactic acid and its derivatives. The catalyst includes metal chloride(s) ($MCl_n$) and tin-containing compound(s). M is selected from a group consisting of $Li^+$, $Na^+$ $K^+$, $Mg^{2+}$, $Ca^{2+}$, $Sr_{2+}$, $Ga^{3+}$, $In^{3+}$, $Sb^{3+}$, $Bi^{3+}$, $Cr^{3+}$, $Mn^{2+}$, $Fe^{2+}$, $Co^{2+}$, $Ni^{2+}$, $Zn^{2+}$, and n represents 1, 2 or 3.

The tin-containing compound(s) includes at least one of $Sn^{4+}$ and $Sn^{2+}$. The anion of the tin-containing compound(s) is selected from a group consisting of $F^-$, $Cl^-$, $Br^-$, $I^-$, $HSO_4^-$, $CH_3SO_3^-$, $C_6H_5SO_3^-$, $H_2PO_4^-$, $HPO_4^{2-}$, $PO_4^{3-}$, $PF_6^-$, $BO_2^-$, $BF_4^-$, $SiF_6^{2-}$ and $CH_3CO_2^-$.

In one embodiment, the tin-containing compound(s) is $SnCl_2$.

In one embodiment, the composite catalyst is a composite of NaCl and $SnCl_2$.

In one embodiment, the composite catalyst is a composite of $CaCl_2$ and $SnCl_2$.

In one embodiment, the composite catalyst is a composite of $MgCl_2$ and $SnCl_2$.

Figure 1:
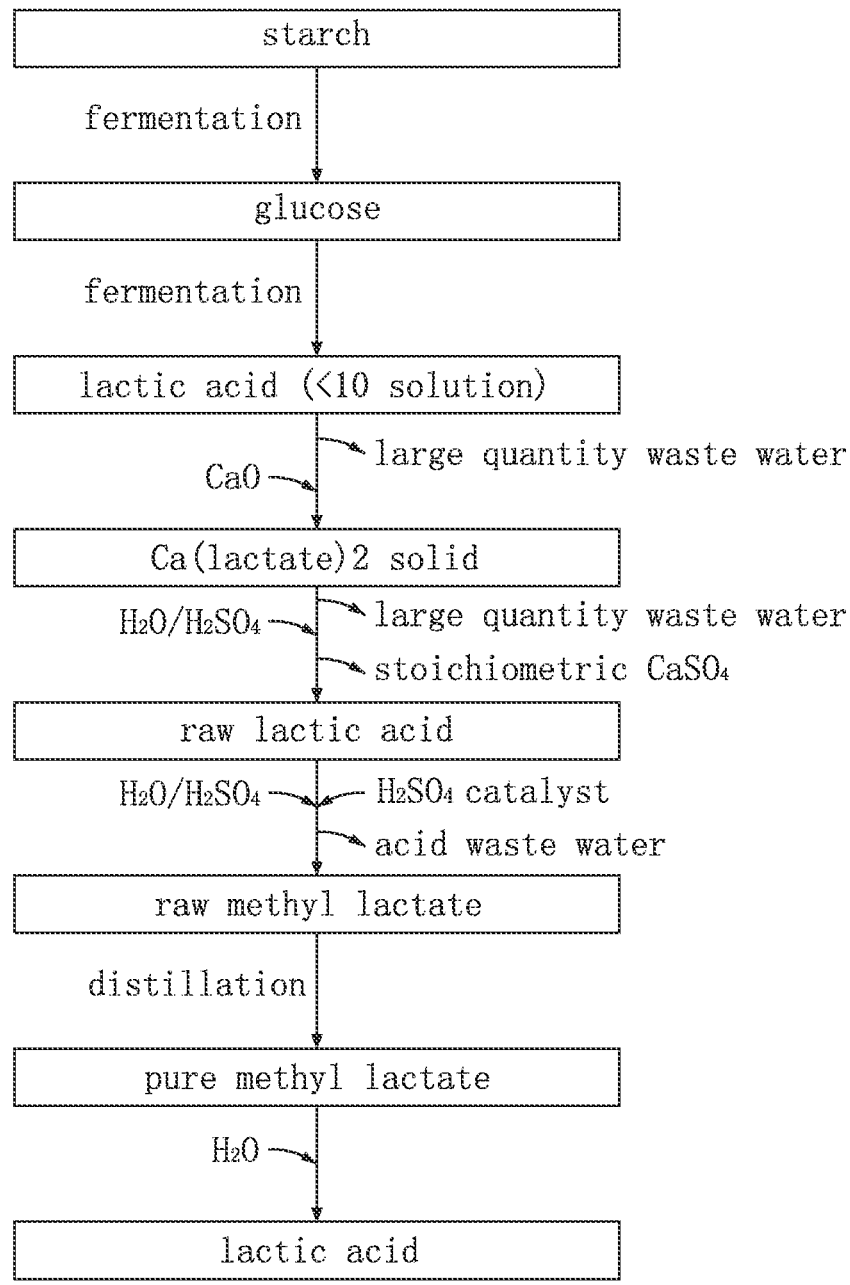
FIG. 1 shows the scheme for lactic acid preparation according to a commercial fermentation process.
Figure 2:
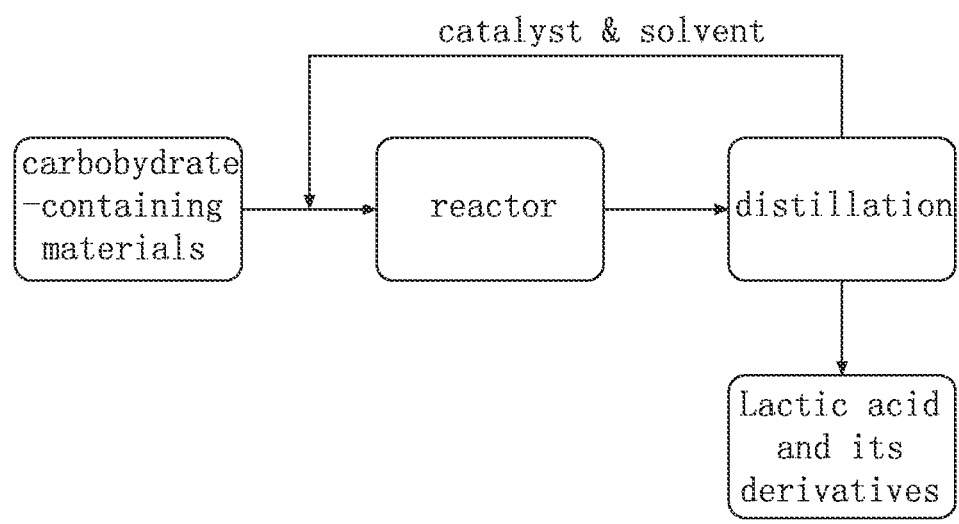
FIG. 2 shows the scheme of a method for synthesis of lactic acid and its derivatives in accordance with an embodiment of the present invention.

This disclosure further provides a method for synthesis of lactic acid and its derivatives. Referring to FIG. 2, in this method, carbohydrate-containing raw material, the above described catalyst, an alcohol and a solvent are added into a reactor, and then heated to carry out the reaction. The obtained solution is distilled to obtain lactic acid and its derivatives such as lactate, and the catalyst can be reused.

The carbohydrate-containing raw material is at least one of polysaccharide and monosaccharide. Moreover, the carbohydrate-containing raw material is at least one selected from a group consisting of cellulose, starch, glucosan, sucrose, fructose and glucose. All substances, which could be converted into carbohydrates by fermentation, hydrolysis or alcoholysis, can be employed as the reactants of the current invention.

The alcohol is selected from the group consisting of monohydric alcohols, dihydric alcohols, and polyhydric alcohols. Further, the monohydric alcohol is selected from at least one of methanol, ethanol, 1-propanol, 2-propanol, 1-butanol, 2-butanol, and tert-butanol. The dihydric alcohol is selected from the group consisting of ethylene glycol, 1,2-propanediol, and 1,3-propanediol. The polyhydric alcohol is glycerol.

A mass ratio of the alcohol to the carbohydrate-containing raw material is in a range from 0.5 to 20, and in other embodiments, the mass ratio of the alcohol to the carbohydrate-containing raw material is further in a range from 1 to 10. In one embodiment, mass ratio of the alcohol to the carbohydrate-containing raw material is about 1.5.

The solvent, for example, is a polar solvent, such as water, alcohols, the methyl esters of C8 to C22 fatty acids, or mixtures thereof, which could dissolve the catalyst to form a homogeneous catalyst solution. For example, the polar solvent is selected from a group consisting of water, methanol, alcohol, 1-propanol, 2-propanol, 1-butanol, 2-butanol, tert-butanol, 1,2-propanediol, 1,3-propanediol and glycerol.

A reaction temperature of the heating step is between 50 and 200° C., and more preferably, the reaction temperature of the heating step is between 80 and 180° C.

In addition, the reaction temperature can be further adjusted according to different composition of the carbohydrate-containing raw material.

In a specific embodiment, the carbohydrate-containing raw material is cellulose and the reaction temperature is between 80 and 180° C.; more preferably, the reaction temperature is between 100 and 180° C.

In a specific embodiment, the carbohydrate-containing raw material is starch and the reaction temperature is between 80 and 180° C.; more preferably, the reaction temperature is between 80 and 160° C.

In a specific embodiment, the carbohydrate-containing raw material is sucrose or glucose and the reaction temperature is between 50 and 180° C.; more preferably, the reaction temperature is between 50 and 140° C.

The above described method employs a non-fermentation technique to process carbohydrate-containing raw material and obtain lactic acid and its derivatives directly. Compared with conventional commercially employed fermentation process, less waste water and solid wastes are produced and thus it is more environment-friendly. In addition, the utilization rate of the carbohydrate-containing raw material is improved and the newly proposed process also has the advantages of simplified steps and low energy consumption, and therefore the method is an economical and efficient method.

EXAMPLE 1

In the reaction, 100.0 g of $SnCl_2 \cdot 2H_2O$ and 163.0 g of $MgCl_2 \cdot 6H_2O$ were added into a reactor (inside volume 10.0 L) as catalyst. Then 3.050 kg of methanol was added into the reactor, and the reactor was sealed and heated to 130° C. under stirring. 511.0 g of water and 500.0 g of sucrose were mixed to obtain a solution, which was pumped into the reactor with a flow of 8.0 mL/min to carry out the reaction. After pumping all of the sucrose aqueous solution, continue more 1.5 hours at 130° C. to complete the reaction. The product was analyzed by gas chromatograph with thermal conductivity detector (GC-TCD) and high-performance liquid chromatography (HPLC). The yield of methyl lactate is 53% and the yield of lactic acid is 33%.

EXAMPLE 2

In the reaction, 100.0 g of $SnCl_2 \cdot 2H_2O$ and 163.0 g of $MgCl_2 \cdot 6H_2O$ were added into a reactor (inside volume 10.0 L) as catalyst. Then 3.005 kg of methanol was added into the reactor, and the reactor was sealed and heated to 120° C. under stirring. 511.0 g of water and 500.0 g of sucrose were mixed to obtain a solution, which was pumped into the reactor with a flow of 8.0 mL/min to carry out the reaction. After pumping all of the sucrose aqueous solution, continue more 1.5 hours at 120° C. to complete the reaction. The product was analyzed by GC-TCD and HPLC. The yield of methyl lactate is 51% and the yield of lactic acid is 39%.

EXAMPLE 3

In the reaction, 100.7 g of $SnCl_2 \cdot 2H_2O$ and 162.8 g of $MgCl_2 \cdot 6H_2O$ were added into a reactor (inside volume 10.0 L) as catalyst. Then 2.998 kg of methanol was added into the reactor, and the reactor was sealed and heated to 130° C. under stirring. 500.0 g of water and 500.0 g of sucrose were mixed to obtain a solution, which was pumped into the reactor with a flow of 8.0 mL/min to carry out the reaction. After pumping all of the sucrose aqueous solution, continue more 0.5 hours at 130° C. to complete the reaction. The product was analyzed by GC-TCD and HPLC. The yield of methyl lactate is 57% and the yield of lactic acid is 29%.

EXAMPLE 4

In the reaction, 100.0 g of $SnCl_2 \cdot 2H_2O$ and 163.0 g of $MgCl_2 \cdot 6H_2O$ were added into a reactor (inside volume 10.0 L) as catalyst. Then 2.998 kg of methanol was added into the reactor, and the reactor was sealed and heated to 130° C. under stirring. 500.0 g of water and 500.0 g of glucose were mixed to obtain a solution, which was pumped into the reactor with a flow of 8.0 mL/min to carry out the reaction. After pumping all of the glucose aqueous solution, continue more 1.5 hours at 130° C. to complete the reaction. The product was analyzed by GC-TCD and HPLC. The yield of methyl lactate is 43% and the yield of lactic acid is 31%.

EXAMPLE 5

In the reaction, 100.0 g of $SnCl_2 \cdot 2H_2O$ and 93.5 g of NaCl were added into a reactor (inside volume 10.0 L) as catalyst. Then 3.021 kg of methanol was added into the reactor, and the reactor was sealed and heated to 130° C. under stirring. 501.5 g of water and 500.0 g of sucrose were mixed to obtain a solution, which was pumped into the reactor with a flow of 8.0 mL/min to carry out the reaction. After pumping all of the sucrose aqueous solution, continue more 1.5 hours at 130° C. to complete the reaction. The product was analyzed by GC-TCD and HPLC. The yield of methyl lactate is 48% and the yield of lactic acid is 28%.

EXAMPLE 6

In the reaction, 100.0 g of $SnCl_2 \cdot 2H_2O$ and 93.6 g of NaCl were added into a reactor (inside volume 10.0 L) as catalyst.

Then 3.046 kg of methanol was added into the reactor, and the reactor was sealed and heated to 130° C. under stirring. 502.4 g of water and 500.0 g of glucose were mixed to obtain a solution, which was pumped into the reactor with a flow of 8.0 mL/min to carry out the reaction. After pumping all of the glucose aqueous solution, continue more 1.5 hours at 130° C. to complete the reaction. The product was analyzed by GC-TCD and HPLC. The yield of methyl lactate is 42% and the yield of lactic acid is 33%.

EXAMPLE 7

In the reaction, 100.0 g of $SnCl_2 \cdot 2H_2O$ and 88.8 g of NaCl were added into a reactor (inside volume 10.0 L) as catalyst. Then 3.004 kg of methanol was added into the reactor, and the reactor was sealed and heated to 130° C. under stirring. 500.0 g of water and 500.0 g of sucrose were mixed to obtain a solution, which was pumped into the reactor with a flow of 8.0 mL/min to carry out the reaction. After pumping all of the sucrose aqueous solution, continue more 1.5 hours at 130° C. to complete the reaction. The product was analyzed by GC-TCD and HPLC. The yield of methyl lactate is 40% and the yield of lactic acid is 26%.

EXAMPLE 8

In the reaction, 100.0 g of $SnCl_2 \cdot 2H_2O$ and 88.8 g of $CaCl_2$ were added into a reactor (inside volume 10.0 L) as catalyst. Then 3.000 kg of methanol was added into the reactor, and the reactor was sealed and heated to 130° C. under stirring. 510.0 g of water and 500.0 g of glucose were mixed to obtain a solution, which was pumped into the reactor with a flow of 8.0 mL/min to carry out the reaction. After pumping all of the glucose aqueous solution, continue more 1.5 hours at 130° C. to complete the reaction. The product was analyzed by GC-TCD and HPLC. The yield of methyl lactate is 37% and the yield of lactic acid is 25%.

EXAMPLE 9

In the reaction, 0.1 g of $SnCl_2 \cdot 2H_2O$ and 0.5 g of $MgCl_2$ were added into a reactor (inside volume 12.0 mL) as catalyst. Then 4.8 g of methanol, 0.2 g of water and 1.2 g of sucrose were added into the reactor, and the reactor was sealed and heated to 70° C. under stirring to carry out the reaction. The reaction was maintained for 4 h. The product was analyzed by GC-TCD and HPLC. The yield of methyl lactate is 13% and the yield of lactic acid is not analyzed.

EXAMPLE 10

In the reaction, 0.1 g of $SnCl_2 \cdot 2H_2O$ and 0.5 g of $MgCl_2$ were added into a reactor (inside volume 12.0 mL) as catalyst. Then 4.8 g of methanol, 0.2 g of water and 1.2 g of sucrose were added into the reactor, and the reactor was sealed and heated to 80° C. under stirring to carry out the reaction. The reaction was maintained for 4 h. The product was analyzed by GC-TCD and HPLC. The yield of methyl lactate is 20% and the yield of lactic acid is not analyzed.

EXAMPLE 11

In the reaction, 0.1 g of $SnCl_2 \cdot 2H_2O$ and 0.5 g of $MgCl_2$ were added into a reactor (inside volume 12.0 mL) as catalyst. Then 4.8 g of methanol, 0.2 g of water and 1.2 g of sucrose were added into the reactor, and the reactor was sealed and heated to 100° C. under stirring to carry out the reaction. The reaction was maintained for 4 h. The product was analyzed by GC-TCD and HPLC. The yield of methyl lactate is 28% and the yield of lactic acid is not analyzed.

The above descriptions are only preferred embodiments of the present invention, and are not intended to limit the present invention. Any amendments, replacement and modification made to the above embodiments under the spirit and principle of the present invention should be included in the scope of the present invention.

What is claimed is:

1. A method for synthesis of lactic acid and its derivatives, comprising:
   providing a mixture, comprising: at least one carbohydrate-containing raw material, at least one alcohol, at least one composite catalyst containing metal chloride(s) (MCln) and tin-containing compound(s), and at least one solvent, wherein M is selected from a group consisting of $Li^+$, $Na^+$ $K^+$, $Mg^{2+}$, $Ca^{2+}$, $Sr^{2+}$, $Ga^{3+}$, $In^{3+}$, $Sb^{3+}$, $Bi^{3+}$, $Cr^{3+}$, $Mn^{2+}$, $Fe^{2+}$, $Co^{2+}$, $Ni^{2+}$, $Zn^{2+}$, and n represents 1, 2 or 3, and the at least one solvent comprises the methyl esters of C8 to C22 fatty acids; and
   heating the mixture to obtain lactic acid and its derivatives.

2. The method for synthesis of lactic acid and its derivatives of claim 1, wherein the tin-containing compound(s) comprises at least one of $Sn^{4+}$ and $Sn^{2+}$.

3. The method for synthesis of lactic acid and its derivatives of claim 2, wherein the anion of the tin-containing compound(s) is selected from a group consisting of $F^-$, $Cl^-$, $Br^-$, $I^-$, $HSO_4^-$, $CH_3SO_3^-$, $C_6H_5SO_3^-$, $H_2PO_4^-$, $HPO_4^{2-}$, $PO_4^{3-}$, $PF_6^-$, $BO_2^-$, $BF_4^-$, $SiF_6^{2-}$ and $CH_3CO_2^-$.

4. The method for synthesis of lactic acid and its derivatives of claim 3, wherein the tin-containing compound(s) is $SnCl_2$.

5. The method for synthesis of lactic acid and its derivatives of claim 1, wherein the carbohydrate-containing raw material is at least one of polysaccharide and monosaccharide.

6. The method for synthesis of lactic acid and its derivatives of claim 5, wherein the carbohydrate-containing raw material is at least one selected from a group consisting of cellulose, starch, glucosan, sucrose, fructose and glucose.

7. The method for synthesis of lactic acid and its derivatives of claim 1, wherein the alcohol is selected from the group consisting of monohydric alcohols, dihydric alcohols, and polyhydric alcohols.

8. The method for synthesis of lactic acid and its derivatives of claim 7, wherein the alcohol is monohydric alcohol, and the monohydric alcohol is selected from a group consisting of methanol, ethanol, 1-propanol, 2-propanol, 1-butanol, 2-butanol, and tert-butanol.

9. The method for synthesis of lactic acid and its derivatives of claim 7, wherein the alcohol is dihydric alcohol, and the dihydric alcohol is selected from the group consisting of ethylene glycol, 1,2-propandiol, and 1,3-propandiol.

10. The method for synthesis of lactic acid and its derivatives of claim 7, wherein the alcohol is polyhydric alcohol, and the polyhydric alcohol is glycerol.

11. The method for synthesis of lactic acid and its derivatives of claim 1, wherein the composite catalyst is a composite of NaCl and $SnCl_2$.

12. The method for synthesis of lactic acid and its derivatives of claim 1, wherein the composite catalyst is a composite of $MgCl_2$ and $SnCl_2$.

13. The method for synthesis of lactic acid and its derivatives of claim 1, wherein the composite catalyst is a composite of $CaCl_2$ and $SnCl_2$.

14. The method for synthesis of lactic acid and its derivatives of claim 1, wherein the solvent further comprises water, and alcohols.

15. The method for synthesis of lactic acid and its derivatives of claim 14, wherein the alcohols is selected from a group consisting of alcohol, 1-propanol, 2-propanol, 1-butanol, 2-butanol, tert-butanol, 1,2-propanediol, 1,3-propanediol and glycerol.

16. The method for synthesis of lactic acid and its derivatives of claim 4, wherein a reaction temperature of the heating step is between 50 and 200° C.

17. The method for synthesis of lactic acid and its derivatives of claim 16, wherein the reaction temperature of the heating step is between 80 and 180° C.

* * * * *